United States Patent [19]

Strommen

[11] Patent Number: 4,703,253

[45] Date of Patent: Oct. 27, 1987

[54] PROBE FOR MONITORING THE CORROSION OF A STEEL REINFORCEMENT MEMBER IN A CONCRETE BODY

[76] Inventor: Roe Strommen, Rydningen 23B, Trondheim, Norway, N-7000

[21] Appl. No.: 772,377

[22] Filed: Sep. 4, 1985

[51] Int. Cl.[4] .................. H01C 17/00; H01C 13/00
[52] U.S. Cl. .................................. 324/65 CR; 338/195
[58] Field of Search .............. 204/1 T, 404, 129.2; 324/65 P, 65 CR, 71.2; 338/195

[56] References Cited

U.S. PATENT DOCUMENTS 3,104,355 9/1965 Holmes ........................... 324/65 Cr

OTHER PUBLICATIONS

Schaschl: "The Effect of Dissolved Oxygen on Corrosion . . . " Corrosion-Natul. Asso. of Corr. Eng.-Oct. 56-pp. 243-251-USCL 204/404.

Primary Examiner—Reinhard J. Eisenzopf
Assistant Examiner—Jose M. Solis
Attorney, Agent, or Firm—James E. Pittenger

[57] ABSTRACT

Probe for monitoring the corrosion of a metallic reinforcement member in a concrete body. Two elements (11,12) of a rodshaped material, preferably in one piece of a material identical to that of the reinforcement member, are joined in a loop. One leg (11) of the loop is acting as an active, corroding element of the probe, while the other leg (12) is covered by a protective sheating (14) of non-corrosive material, the loop being provided to be connected to an electric circuit for measuring the electrical resistance of the legs. In operative condition, the probe is embedded in the concrete body, electrically insulated from the reinforcement member.

4 Claims, 1 Drawing Figure

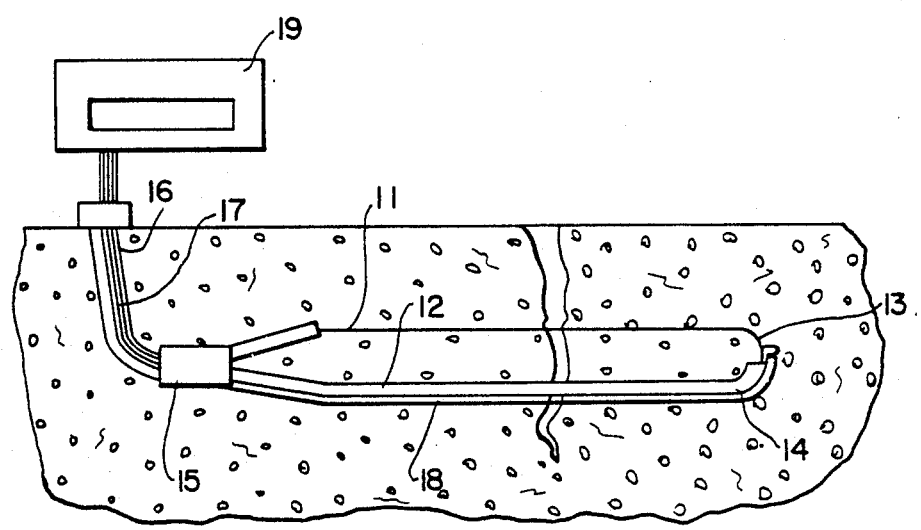

PROBE FOR MONITORING THE CORROSION OF A STEEL REINFORCEMENT MEMBER IN A CONCRETE BODY

This invention relates to a probe for monitoring the corrosion of a steel reinforcement member embedded in a concrete body, particularly in a concrete body in a corrosive environment, e.g. offshore. More specifically, the invention relates to a probe of the kind described in the introductory part of claim 1.

It is known to provide probes with an exposed member and a separately arranged reference member. By measuring the resistance of the exposed part of the probe with certain intervals, it is possible to monitor impaired properties due to corrosion and thus have a measure for the corrosive effect. By comparing the measured resistance with the resistance of the reference element, it is possible to compensate for any change in temperature, which would otherwise make the measurements unreliable.

It is an object of the present invention to provide an improved probe, suitable for embedding in a concrete body electrically insulated relatively to the reinforcement member. It is a further object to provide a probe which can measure a corrosive effect as close to the actual corrosion as possible. It should have a simple construction and be easy to mount.

According to the invention, this may be achieved by providing a probe according to the patent claim 1.

This probe will be influenced by the corrosion very closely to the corrosion on a reinforcement member. Due to its simple structure and easy mounting, it can be introduced on multiple locations with reasonable costs.

Claims 2 and 3 describe two advantageous features of a probe according to the invention. The feature of claim 2 will simplify the manufacturing and mounting and the feature of claim 3 will ensure an advantageous cost-accuracy relationship.

The invention is further described hereinafter, by way of an example, with reference to the accompanying drawing which illustrates a preferred form of the present invention. The figure shows a side view of an embodiment of the invention embedded in a concrete body.

The probe of the embodiment shown comprises a loop consisting of two parallel legs 11 and 12, respectively, of a material normally used for reinforcing concrete, i.e. a steel rod with a diameter of 6–12 mm. Said two legs 11 and 12 are joined at one end with an integral web 13 of the same material. The loop is preferably manufactured by bending a rod of reinforcement steel. The leg 12 is covered by a protectiv sheating 14 of a syntetic material, such as an electrically insulating elastomer. The free ends of the legs 11 and 12, as well as the corresponding end of the sheating 14, are embedded in an electrically insulating block 15 serving as a housing to the electrical connection of the legs 11 and 12 to connecting wires 16 and 17 respectively. The connection between said two legs 11 and 12, i.e. the web 13, is connected to a third electrical wire 18. The wires 16, 17 and 18 are connected to a measurement and monitoring circuit shown schematically at 19. This circuit can be of a suitable design principally known in this field.

The described embodiment can be modified in various ways. The loop may comprise two legs being joined electrically conductive at one end with a connection member. The shape of the loop may be different from that shown, e.g. curvilinear, to be adapted to embedding in a cylindrical column.

The covering sheathing 14 of the reference member 12 can be provided by various techniques known in the art.

I claim:

1. Probe for monitoring the corrosion of a steel reinforcement member embedded in concrete, said probe comprising an exposed metal element liable to corrode and arranged to be introduced in an electric circuit to measure the electric resistance of the element, the exposed probe element is a first part of a rodshaped member of a diameter and a material the same as the reinforcement member the corrosion of which is to be monitored, a second part of the rodshaped member being a reference element protected against corrosion by a suitable sealing means, said second part to be electrically connected in the electrical circuit as a temperature compensating element;

the ends of the first and second parts of the rodshaped member and the common area between these parts being connected by individual electric wires which connect the member to the resistance measuring circuit; and the ends of the first and second parts of the rodshaped member and their wire connections are embedded in an insulating material which encapsulates the connections and supports the member while the concrete is setting.

2. Probe according to 1, characterized in that the rodshaped member is curvilinear.

3. Probe according to claim 1, characterized in that the rodshaped member is formed as a loop with two substantially parallel legs.

4. Probe according to claim 1, characterized in that each leg of the rodshaped member has a length within a range of 3 to 20 ft., said two legs being of substantially the same length.

* * * * *